United States Patent [19]

Gerzon et al.

[11] 4,362,664

[45] Dec. 7, 1982

[54] VINBLASTINE OXAZOLIDINEDIONE DISULFIDES AND RELATED COMPOUNDS

[75] Inventors: Koert Gerzon; Jean C. Miller, both of Indianapolis, Ind.

[73] Assignee: Eli Lilly and Company, Indianapolis, Ind.

[21] Appl. No.: 220,472

[22] Filed: Dec. 29, 1980

[51] Int. Cl.$^3$ ............... C07D 519/04; A61K 31/475
[52] U.S. Cl. .................................. 260/244.4; 424/262
[58] Field of Search .................... 250/244.4; 424/262

[56] References Cited

U.S. PATENT DOCUMENTS

| Re. 30,560 | 3/1981 | Miller et al. | 260/244.4 |
| 4,096,148 | 6/1978 | Miller et al. | 260/244.4 |
| 4,199,504 | 4/1980 | Conrad et al. | 260/244.4 |
| 4,203,898 | 5/1980 | Cullinan et al. | 260/244.4 |

OTHER PUBLICATIONS

Barnett et al., J. Med. Chem., 21, pp. 88–96 (1978).
Conrad et al., J. Med. Chem. 22, pp. 391–400 (1979).
McOmie, ed., Protective Groups in Organic Chemistry, Plenum Press, London & New York, 1973, pp. 236, 238.

*Primary Examiner*—Donald G. Daus
*Assistant Examiner*—Diana G. Rivers
*Attorney, Agent, or Firm*—James L. Rowe; Arthur R. Whale

[57] ABSTRACT

Thioalkyl derivatives of vinblastine 3-spiro-5''-oxazolidine-2'',4''-dione, mitotic inhibitors.

6 Claims, No Drawings

VINBLASTINE OXAZOLIDINEDIONE DISULFIDES AND RELATED COMPOUNDS

BACKGROUND OF THE INVENTION

The alkaloids obtainable from *Vinca rosea* (*Catharanthus rosea*) have constituted a most productive source for drugs which adversely affect the growth of experimental malignancies in mammals. Initially, only some of the alkaloids obtainable from the leaves of the plant by extraction and purifiable by chromatography were found to be active. It has been found that all these active anti-neoplastic Vinca alkaloids obtained directly from the plant are dimeric indole-dihydroindole alkaloids which can be represented by the formula:

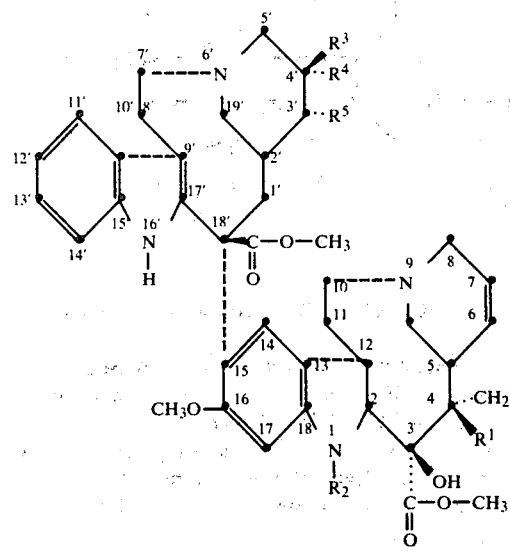

In the above formula where $R^1$ is acetoxy, $R^2$ is methyl, $R^3$ is hydroxyl, $R^4$ is ethyl and $R^5$ is H, vinblastine (vincaleucoblastine, VLB) is represented; where $R^1$ is acetoxy, $R^2$ is formyl, $R^3$ is hydroxyl, $R^4$ is ethyl and $R^5$ is H, vincristine (leurocristine) is represented; where $R^1$ is acetoxy, $R^2$ is methyl, $R^3$ is ethyl, $R^4$ is hydroxy, and $R^5$ is H, leurosidine is represented; where $R^1$ is acetoxy, $R^2$ is methyl or formyl, $R^3$ is ethyl and $R^4$ and $R^5$ taken together form an α-epoxide ring, leurosine and leuroformine, respectively are represented. Literature references to the above alkaloids are as follows: leurosine (U.S. Pat. No. 3,370,057), VLB (U.S. Pat. No. 3,097,137), leuroformine (Belgian Pat. No. 811,110); leurosidine (vinrosidine) and vincristine (both in U.S. Pat. No. 3,205,220).

Two of the above alkaloids, vinblastine and vincristine, are now marketed for the treatment of malignancies, particularly the leukemias and related diseases, in humans. The two marketed alkaloids are customarily administered by the iv route. Two others, leurosidine and leuroformine, have been on clinical trial in the United States or in Europe.

Chemical modification of the Vinca alkaloids started slowly for several reasons. In the first place, the molecular structures involved are extremely complex, and chemical reactions which modify one specific functional group of the molecule without affecting other groups have been difficult to develop. Secondly, dimeric alkaloids lacking desirable chemotherapeutic properties have been recovered or produced from *Vinca* *rosea* extracts, and a determination of their structures has led to the conclusion that these inactive compounds are closely related structurally to, or even isomeric with, an active alkaloid.

One of the more recent, and more successful, modifications of the basic indole-dihydroindole structure has been the preparation of C-3 carboxamide and carboxhydrazide derivatives. Many of these carboxamides are active anti-tumor agents (see U.S. Pat. No. 4,166,810, Barnett et al., J. Med. Chem., 21, 88 (1978), id, 22, 391 (1979). In particular, 4-desacetyl VLB C-3 carboxamide (vindesine) is very active and is currently on clinical trial in humans.

A related approach is described in United States patent 4,096,148 wherein the preparation of various unsubstituted or substituted 3-spiro-5''-oxazolidine-2'',4''-dione derivatives of VLB, desacetyl VLB and 4-desacetyl vincristine are described among other compounds. Typical Vinca oxazolidinedione derivatives found in the above patent can be portrayed by the following formula

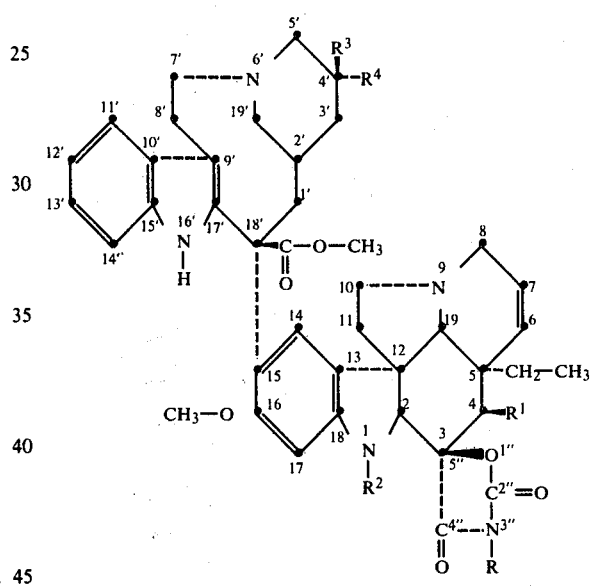

wherein
R is H, $C_1$-$C_4$ alkyl, $C_3$-$C_4$ alkenyl, $CH_2$—CHX—$CH_3$ or $CH_2$—$CH_2$X;
wherein
X is Br or Cl;
$R^1$ is OH or

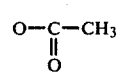

$R^2$ is $CH_3$ or CHO;
one of $R^3$ and $R^4$, is OH or H and the other is $C_2H_5$.

According to U.S. Pat. No. 4,096,148, these oxazolidinediones are prepared by reaction of, for example, vinblastine with an isocyanate RNCO (where R is other than H). One of the compounds thus prepared is 3''-(2-chloroethyl)-3-spiro-5''-oxazolidine-2'',4''-dione. This compound has proved to be an extremely active antineoplastic agent but is also described in the aforesaid patent as being useful as an intermediate—see Col. 7 lines 49–58—for the preparation of the corresponding 3''-(2-thioethyl) derivative. This latter compound is stated to be, in turn, useful as an intermediate in preparing the corresponding N-(β-thioethyl)VLB 3-carboxamide (compound 25 in Conrad et al., loc. cit.).

It is an object of this invention to find improved methods for synthesizing VLB 3''-(β-thioethyl)-3-spiro-5''-oxazolidine-2'',4''-dione.

DESCRIPTION OF THE INVENTION

This invention provides an improved method of preparing compounds of the formula

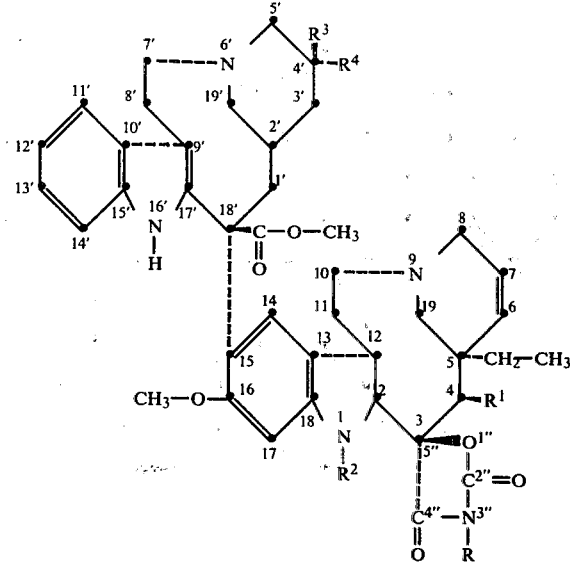

wherein one of $R^3$ and $R^4$ is OH or H and the other is ethyl; $R^2$ is $CH_3$ or CHO; $R^1$ is OH or acetoxy and R is $C_2H_4SR^5$ wherein $R^5$ is H or $CH_3$. Also provided are new intermediates of the structure:

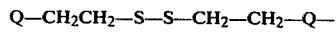
Q—CH$_2$CH$_2$—S—S—CH$_2$—CH$_2$—Q—

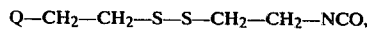
Q—CH$_2$—CH$_2$—S—S—CH$_2$—CH$_2$—NCO, and

Q—CH$_2$—CH$_2$—S—S—CH$_2$—CH$_2$—NH—CO$_2$alk wherein alk is (C$_1$-C$_3$)alkyl and Q is all of II except the R group at C-3'' of the oxazolidinedione ring. Q can be represented by III below.

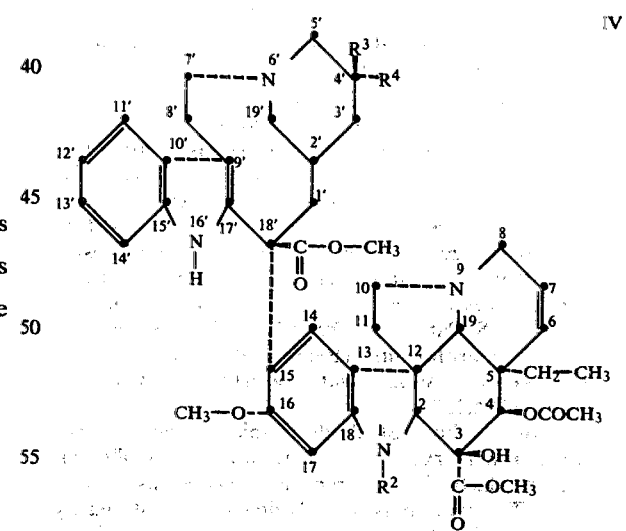

wherein $R^1$, $R^2$, $R^3$ and $R^4$ have the same meaning as hereinabove.

Also provided by this invention are new isocyanates of the formula OCN—CH$_2$—CH$_2$—S—R$^6$ wherein $R^6$ is $CH_3$ or —S—CH$_2$—CH$_2$—NCO.

The 3''-thioalkyl oxazolidinediones represented by II above and by (Q—CH$_2$CH$_2$S—)$_2$ are prepared the following reaction: a Vinca dimer of the structure

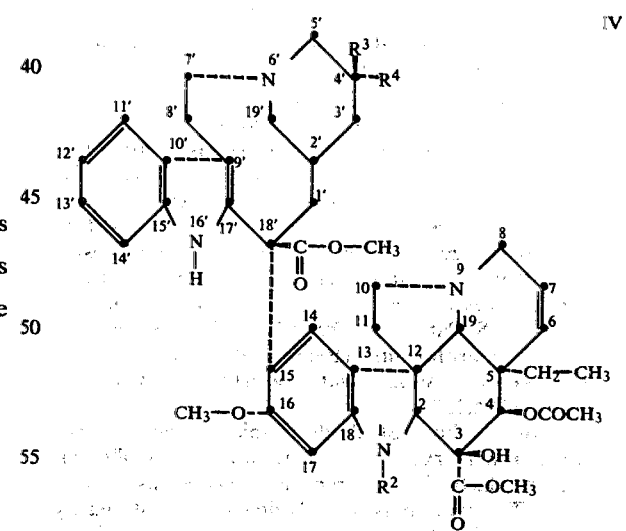

wherein $R^2$, $R^3$ and $R^4$ have their previously assigned meaning, is reacted with an isocyanate of the structure OCN—CH$_2$—CH$_2$—S—R to yield an oxazolidinedione according to formula II above in which R is CH$_2$—CH$_2$—S—CH$_3$, or an intermediate according to III above in which R is CH$_2$—CH$_2$—S—S—CH$_2$—CH$_2$—N=C=O. This latter compound is not isolated as such ordinarily but as a reaction product with a lower alkanol —(C$_1$-C$_3$)alkylOH—; having structure II wherein R is CH$_2$—CH$_2$—S—S—CH$_2$—CH$_2$—NH—CO—O—(C$_1$-C$_3$)alkyl and R$^1$ is acetoxy.

Reduction of the Vinca tetramer disulfide Q—CH$_2$—CH$_2$—S—S—CH$_2$—CH$_2$—Q or of an intermediate Vinca dimer disulfide [III wherein R$^1$ is acetoxy and R is CH$_2$—CH$_2$—S—S—CH$_2$—CH$_2$—NCO or CH$_2$—CH$_2$—S—S—CH$_2$—CH$_2$—NH—CO—O—(C$_1$-C$_3$)alkyl], with zinc and acetic acid or other appropriate reducing agent yields the 3″-($\beta$-thioethyl)oxazolidine dione (III wherein R is CH$_2$—CH$_2$—SH). Oxidation of this thioethyl oxazolidinedione with ferrocyanide or other suitable oxidizing agent having an E$_0$ of about +0.50 yields a Vinca tetramer disulfide (Q—CH$_2$CH$_2$—S—)$_2$.

In the above reaction involving a Vinca dimer IV and an isocyanate, the secondary hydroxyl at C-4 is acetylated. A 4-hydroxy if present, would react with the isocyanate. It can be protected other than by acetylation, however.

It is believed that the formation of the oxazolidinedione ring starts with the reaction of the 3-hydroxy with an isocyanate to form a carbamate which, in a second step, cyclizes to an oxazolidinedione ring with loss of CH$_3$OH.

The 3″-thioalkyl oxazolidinediones represented by III when R is CH$_2$—CH$_2$—SH or CH$_2$—CH$_2$—S—CH$_3$ and by (Q—CH$_2$—CH$_2$—S—)$_2$ are active antimitotic and antineoplastic agents in their own right, but can also be converted by mild alkaline hydrolysis to carboxamide derivatives of VLB, vincristine, leurosidine etc. and of the corresponding 4-desacetyl compounds (structure IV wherein The C-4

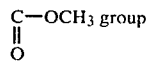

C—OCH$_3$ group is replaced by a

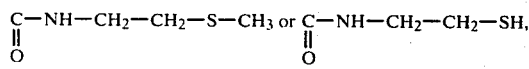

and the corresponding disulfide—see Conrad et al., loc. cit—compounds 25, 26, 30 and 37 and U.S. Pat. No. 4,096,148, col. 7, line 32 et seq).

This invention is further illustrated by the following specific examples.

EXAMPLE 1

Preparation of Vinblastine 3″-($\beta$-[$\beta$-(methoxycarbonylamino)ethyldithio]ethyl)-3-spiro-5″-oxazolidine-2″,4″-dione A solution was prepared from 40.4 g. of p-nitrophenylchloroformate and 150 ml. of acetonitrile. This solution was added to a slurry of 22.5 g. of cystamine dihydrochloride and 150 ml. of anhydrous acetonitrile. The reaction mixture was heated to refluxing temperature for about 2 days after which time it was cooled and filtered. The filter cake comprising cystamine-bis-carbamate was crystallized from hot toluene. The crystalline product was then stirred with water for one-half hour to remove unreacted cystamine. This aqueous mixture was filtered and the precipitate washed with water. Yield of cystamine-bis(p-nitrophenyl)-carbamate was 19.5 g. melting at 163°-165° C.

nmr (DMSO-d$_6$): 2.91 (4H, t), 3.46 (4H, t), 3.82 (2H bis, exchangeable with D$_2$O), 7.41 (4H, d), 8.26 (4H, d) $\delta$.

Infrared spectrum (mull); 3360, 1710, 1350, 1215 cm$^{-1}$.

Mass spectrum: m/e 204 (loss of carbamate from molecular ion plus fragmentation of the disulfide bond).

Analysis Calculated for: C$_{18}$H$_{18}$N$_4$O$_8$S$_2$:

Theory: C, 44.81; H, 3.76; N, 11.61; S, 13.29.

Found: C, 45.05; H, 3.97; N, 11.80; S, 13.55.

Seven and nine-tenths grams of cystamine-bis(p-nitrophenyl)carbamate and 2.9 g. of triethylamine were dissolved in toluene and the resulting solution heated to 40° C. This solution was added in dropwise fashion to a solution of 3.1 g. of trimethylsilylchloride in 25 ml. of toluene. The resulting mixture was heated to 90° C. for about 3 hours, and was then cooled. Triethylamine hydrochloride precipitated and was separated by filtration. The filtrate, containing cystamine-bis-isocyanate formed in the above reaction, was concentrated to about 20 ml. 4.8 G. of vinblastine free base were dissolved in the toluene solution containing the isocyanate. This reaction mixture was heated to about 60° C. for about 10 hours, followed by a heating period of 3 hours at about 80° C. Volatile constituents of the reaction mixture were then removed by evaporation in vacuo leaving 13.7 g. of an oil. This residual oil was chromatographed over 475 g. of silica gel (Woelm activity I). The following eluants were used, based on a 1:1 mixture of methylenedichloride and ethylacetate: 4 l. containing 5% methanol, one l. containing 7.5% methanol, 2 l. containing 10% methanol and 3 l. containing 15% methanol. Fractions shown by tlc to contain vinblastine 3″-($\beta$-[$\beta$-(methoxycarbonylamino)ethyldithio]ethyl)-3-spiro-5″-oxazolidine-2″,4″-dione were combined and the solvent removed from the combined products in vacuo. Purified vinblastine 3″-($\beta$-[$\beta$-(methoxycarbonylamino)ethyldithio]-ethyl)-3-spiro-5″-oxazolidinedione thus prepared (1.24 g.) had the following physical characteristics:

Mass spectrum: m/e 895, 882, 865, 835, 804, 792, 649, 343, 525, 494, 355, 154; field desorption 1014, 882.

nmr (CDCl$_3$): 0.68 (3H, t), 0.89 (3H, t), 2.02 (3H, s, NMe), 3.60 (3H, s, CO$_2$Me), 3.66 (4H, CH$_2$CH$_2$S), 3.79 (3H, s, MeOAr), 5.26 (1H, m, C-6), 5.41 (1H, s, C-4), 5.89 (1H, m, C-7), 6.11 (1H, s, C-17), 6.65 (1H, s, C-14), 7.2-7.5 (4H, m, Ar), 8.15 (1H, br s, NH) $\delta$.

Infrared spectrum: 3600, 3460, 1814 (oxazolidinedionecarbonyl), 1745, 1725, 1700 cm$^{-1}$.

cmr (CDCl$_3$): 154.6, 157.1, 169.8 $\delta$ (new carbonyls due to oxazolidinedione carbamate)

EXAMPLE 2

Preparation of Vinblastine 3″-($\beta$-thioethyl)-3-spiro-5″-oxazolidine-2″,4″-dione A solution was prepared from 507.1 mg. of vinblastine 3″-($\beta$-[$\beta$-(methoxycarbonylamino)ethyldithio]ethyl)-3-spiro-5″-oxazolidine-2″,4″-dione sulfate and 20 ml. of glacial acetic acid. 317.7 Mg. of zinc dust were added and the resulting mixture heated to refluxing temperature for about 1.5 hours. At this time, tlc showed that the reaction had gone essentially to completion. Ice was added to the reaction mixture followed by dilute aqueous ammonium hydroxide to pH=8. Water was added and the resulting aqueous mixture extracted 6 times with an equal volume of methylenedichloride. The methylenedichloride extracts were combined and filtered and the solvent removed from the filtrate by evaporation *in vacuo*. The resulting residue was dried with a toluene azeotrope. Yield of vinblastine 3"-(β-thioethyl)-3-spiro-5"-oxazolidine-2",4"-dione thus prepared was 391.9 mg. The compound had the following characteristics:

nmr (CDCl$_3$): 0.67 (3H, t), 0.88 (3H, t), 2.01 (3H, s), 2.81 (m), 2.84 (3H, s), 3.61 (3H, s), 3.68 (s), 3.79 (3H, s), 4.0 (m), 5.18 (1H, m), 5.45 (1H, s), 5.88 (1H, s), 6.10 (1H, s), 6.64 (1H, s), about 7.5 (4H, m), 8.12 (1H, brs) δ.

Mass spectrum: m/e 895 (transmethylation), 881, 864, 850, 822, 820, 792, 650, 543, 381, 354, 154, 135.

Infrared spectrum (CHCl$_3$): 3670, 3590, 3450, 1815, 1740, 1715, 1615 cm$^{-1}$.

pK$_a$ in 66% aqueous DMF = 5.2, 7.0, 11.1.

The product was converted to the sulfate salt by standard procedures.

EXAMPLE 3

Preparation of
Bis-[β-(vinblastine-3-spiro-5"-oxazolidine-2",4"-dione-3"-yl)ethyl]disulfide A solution containing 327.6 mg. of vinblastine 3"-(2-thioethyl)-3-spiro-5"-oxazolidine-2",4"-dione free base in about 2 ml. of water was prepared by adding sufficient 12 N aqueous hydrochloric acid to solubilize the base. 375.1 Mg of potassium ferricyanide were added. There was an immediate heavy percipitate. The reaction mixture was diluted with 30 ml. of water and the pH adjusted to about 8 by the addition of 14 N aqueous ammonium hydroxide. The resulting aqueous mixture was extracted 5 times with an equal volume of methylenedichloride. The methylenedichloride extracts were combined. The combined extracts were concentrated by evaporation in vacuo and dried with a toluene azeotrope. The residue containing bis-[β-vinblastine-3-spiro-5"-oxazolidine-2",4"-dione-3"-yl)ethyl]-disulfide (weight = 331.7 mg.) was chromatographed over 35 g. of silica (Woelm activity 1). The chromatogram was developed by employing 300 ml. fractions of a 1:1 ethylacetate-methylenedichloride solvent mixture containing increasing amounts of methanol from 4% up to 45%. Fractions shown by tlc to contain the desired disulfide (R$_f$=0.25 in a 3:1 ethylacetate-ethanol solvent mixture) were combined and the solvent removed: yield = 55.9 mg. The compound had the following physical properties:

nmr (CDCl$_3$): 0.68 and 0.89 (12H, 2t), 2.03 (6H, s, OAc), 2.85 (6H, s, NMe), 5.08 (2H, m), 6.11 (2H, s), 6.65 (2H, s), 7.1–7.5 (4H, m, Ar), 8.21 (2H, br s) δ.

Infrared spectrum (CHCl$_3$): 3680, 3600, 3460, 1815, 1745, 1720 (shoulder) cm$^{-1}$.

Mass spectrum: m/e 835 (cleavage of disulfide and loss of CH$_2$S), 817, 804, 775, 592, 494, 355, 154; field desorption 881.

Osmometric weight determination = 2275 (theoretical 1760).

The sulfate salt was prepared by the usual procedure.

As previously stated, the compounds of this invention are antimitotics, and can adversely affect the growth of malignant cells. This activity is manifested in a standard mitotic inhibition test employing Chinese hamster ovary cells.

Table 1 gives the results of this test for the compounds of this invention. In the Table, column 1 gives the name of the compound, column 2 gives the dose in mcg/ml for accumulation in mitosis and column 3, the percent mitotic accumulation as a range.

TABLE 1

| Name of Compound | Dose | Range |
| --- | --- | --- |
| Vinblastine 3"-(β-(β-methoxycarbonylamino)ethyldithio]ethyl)-3-spiro-5"-oxazolidine-2",4"-dione | 20–2 | 7–10 |
| vinblastine 3"-(β-thioethyl)-3-spiro-5"-oxazolidine-2",4"-dione | 20–2 | 10–15 |

The bases of this invention and their salts preparable by the processes disclosed herein are active also in vivo against some but not all transplanted tumors in mice. To demonstrate such activity, a protocol was used involving the administration of the drug by the intraperitoneal or oral route, at selected dose levels, against 6C$_3$ HED lymphosarcoma, B16 melanoma, 755 adenocarcinoma and C$_3$H mammary carcinoma.

The following table—Table 2—gives the results of this experiment in which mice bearing the transplanted tumor were treated with a compound of this invention. In the table, column 1 gives the name of the compound; column 2, the name of the tumor; column 3, the dosage given; and column 4, the percent inhibition of tumor growth (I) or prolongation of life (PL). The following dosage regimen was employed: every fourth day (three doses) starting on the first day after inoculation.

TABLE 2

| Name of Compound | Tumor | Dose (mg/kg) | Percent Inhibition or Prolongation |
| --- | --- | --- | --- |
| vinblastine 3"-(β-[β-(methoxycarbonylamino)ethyldithio]ethyl)-3-spiro-oxazolidine 2",4"-dione | 6C$_3$HED | 2.5 | 12*(I) |
|  | P1534(J) | 2.5 | 16*(I) |
|  | P388/V | 2.5 | 38(PL) |
|  |  | 2.0 | 25*(PL) |
|  |  | 1.5 | 30(PL) |
| vinblastine 3"-(β-thioethyl)-3-spiro-5"-oxazolidine-2",4"-dione | 6C$_3$HED | 2.5 | 14*(I) |
|  | P1534(J) | 2.5 | 14*(I) |
|  | P388/V | 2.5 | 22*(PL) |
| bis-[β-(vinblastine 3-spiro-5"-oxazolidone-2",4"-dione-3"-yl)ethyl]disulfide | 6C$_3$HED | 2.5 | 46(I) |
|  | P1534(J) | 2.5 | 16*(I) |
|  | P388/J | 2.5 | 18*(PL) |
| 4-desacetyl vinblastine 3"-(β-thioethyl)-3-spiro-5"-oxazolidine-2",4"-dione | P388 | 1.4 | 77(PL) |
|  |  | 1.2 | 65(PL) |
|  |  | 1.0 | 52(PL) |

In the above Table, 6C$_3$HED is a lymphosarcoma and P1534(J) and P388/J are leukemias.
*Percentages below 30 are not statistically significant.

In utilizing the novel compounds of this invention as anti-tumor agents in mammals, either the parenteral or oral route of administration may be employed. For such use, the drug is customarily mixed with a pharmaceutically suitable carrier. With parenteral administration, the intravenous route is preferred although, with smaller mammals such as mice, the intraperitoneal route may be used. For intravenous administration, isotonic solutions containing about 1 mg./ml. of a salt of an alkaloidal base of formula II above are employed. The drug is administered at a dose of from 0.01 to 10 mg./kg. of mammalian body weight once or twice a week or every two weeks depending on both the activity and the toxicity of the drug. An alternative method of arriving at a therapeutic dose is based on body surface area with a dose in the range 0.1 to 10 mg./meter squared of mammalian body surface administered every 7 or 17 days or twice weekly.

As would be expected, the compounds of this invention differ in their anti-tumor spectrum from that of VLB, vincristine and vindesine in the same way that the anti-tumor spectra of those compounds differ among themselves, one drug being more effective against certain tumors or classes of tumors and less effective against others. However, in utilizing the compounds of this invention clinically, an oncologist would administer one of them initially by the same route in the same vehicle and against the same types of tumors as employed clinically with vindesine, vincristine and VLB. Differences in dosage level would, of course, be based on relative oncolytic potency and toxicity.

We claim:

1. A compound of the formula

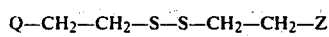

wherein Q is a 3''-oxazolidindionyl radical of the formula:

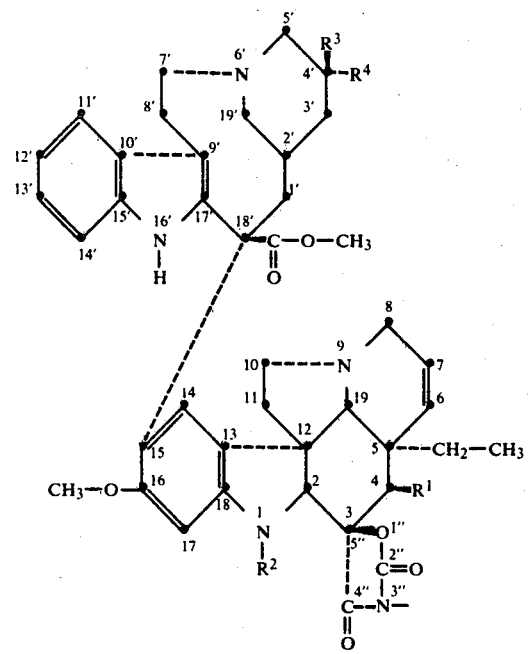

wherein $R^2$ is CHO or $CH_3$; one of $R^3$ and $R^4$ OH or H and the other is ethyl; and Z is Q, NCO or $NH-CO_2-(C_1-C_3)$alkyl.

2. An oxazolidinedione of the formula:

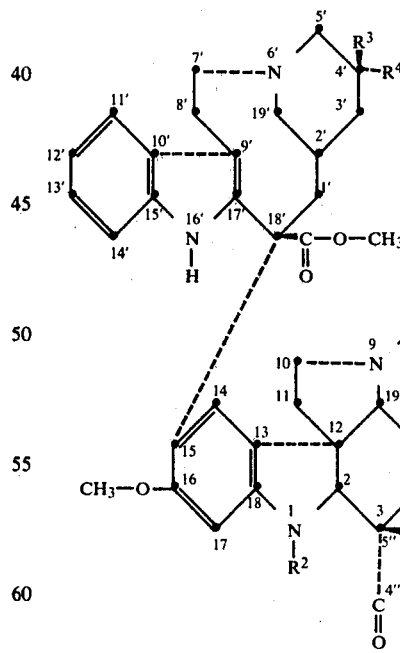

wherein one of $R^3$ and $R^4$ is OH or H and the other is ethyl; $R^2$ is $CH_3$ or CHO; $R^1$ is OH or acetoxy and R is $CH_1-CH_2-S-S-CH_2-CH_2-R^9$ wherein $R^9$ is NCO or $NH-CO-O-(C_1-C_3)$alkyl.

3. A process for preparing a compound of the structure

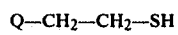

wherein Q is a 3''-oxazolidinedioxyl radical of the formula wherein $R^1$ is OH or acetoxy; $R^2$ is $CH_3$ or CHO; and one of $R^3$ and $R^4$ is H or OH and the other is ethyl, which comprises reducing a compound of the formula $Q-CH_2-CH_2-S-S-CH_2-CH_2-Z$, wherein Z is Q, NCO or $NH-CO_2-(C_1-C_3)$alkyl; and wherein $R^1$ is acetoxy with zinc and acetic acid; and then, to produce a compound in which $R^1$ is OH, subjecting the reduced compound to mild alkaline hydrolysis.

4. The process which comprises oxidizing a compound of the structure Q—CH$_2$—CH$_2$—S—H wherein Q is a 3"-oxazolidinedionyl radical of the formula

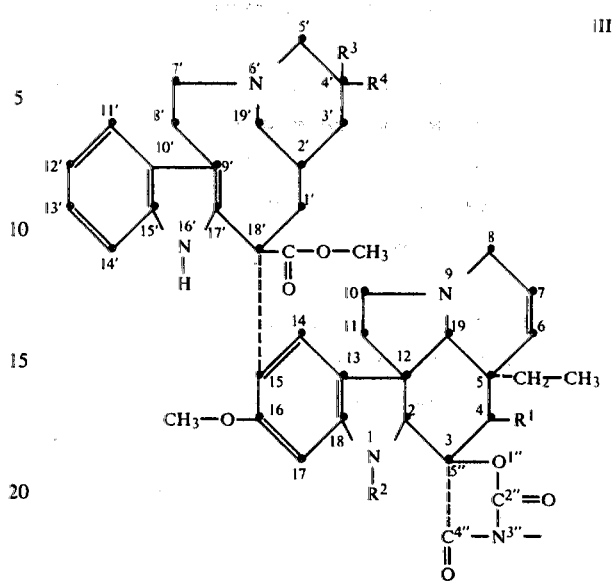

wherein
$R^2$ is CH$_3$ or CHO; $R^1$ is OH or acetoxy and one of $R^3$ and $R^4$ is H or OH and the other is ethyl;
with ferricyanide in hydrochloric acid.

5. A compound according to claim 1, said compound being vinblastine 3"-(β-[β-(methoxycarbonylamino)-ethyldithio]ethyl)-3-spiro-5"-oxazolidine-2",4"-dione.

6. A compound according to claim 1, said compound being vinblastine 3"-(β-[β-isocyanatoethyldithio]ethyl)-3-spiro-5"-oxazolidine-2",4"-dione.

* * * * *